United States Patent
Davies

(10) Patent No.: US 7,432,376 B2
(45) Date of Patent: Oct. 7, 2008

(54) TROPANE PRODRUGS WITH CENTRAL NERVOUS SYSTEM ACTIVITY

(75) Inventor: Huw M. L. Davies, E. Amherst, NY (US)

(73) Assignee: Research Foundation of State University of New York, The, Amherst, NY (US)

( * ) Notice: Subject to any disclaimer, the term of this patent is extended or adjusted under 35 U.S.C. 154(b) by 25 days.

(21) Appl. No.: 11/716,817

(22) Filed: Mar. 12, 2007

(65) Prior Publication Data

US 2007/0232646 A1   Oct. 4, 2007

Related U.S. Application Data

(60) Provisional application No. 60/781,245, filed on Mar. 10, 2006.

(51) Int. Cl.
*C07D 451/02* (2006.01)
(52) U.S. Cl. ...................................................... 546/124
(58) Field of Classification Search ................. 546/124
See application file for complete search history.

(56) References Cited

U.S. PATENT DOCUMENTS

| | | | |
|---|---|---|---|
| 5,227,385 A | 7/1993 | Caldwell et al. |
| 5,262,428 A | 11/1993 | Davies et al. |
| 5,288,872 A | 2/1994 | Davies et al. |
| 5,342,949 A | 8/1994 | Davies et al. |
| 5,591,854 A | 1/1997 | Davies |
| 5,760,055 A | 6/1998 | Davies |
| 5,763,455 A | 6/1998 | Davies et al. |
| 6,008,227 A | 12/1999 | Davies et al. |
| 6,013,242 A | 1/2000 | Davies et al. |

OTHER PUBLICATIONS

Kozkowski et al., Bioorganic & Medicinal Chemistry Letters (1993), 3(6), pp. 1327-1332.*
Davies et al., Synthesis of methylphenidate analogues and their binding affinities at dopamine and serotonin transport sites. Bioorganic & Medicinal Chemistry Letters 14 (2004) 1799-1802.

* cited by examiner

*Primary Examiner*—D. Margaret Seaman
*Assistant Examiner*—Niloofar Rahmani
(74) *Attorney, Agent, or Firm*—Hodgson Russ LLP

(57) ABSTRACT

Disclosed are tropane-based prodrug compounds bearing fatty ester and aromatic substituents. The compounds can be used for alleviating symptoms of CNS disorders.

8 Claims, No Drawings

TROPANE PRODRUGS WITH CENTRAL NERVOUS SYSTEM ACTIVITY

This application claims priority to U.S. patent application Ser. No. 60/781,245, filed on Mar. 10, 2006, the entire disclosure of which is incorporated herein by reference.

This work was supported by Grant Nos. NO1 DA-18826 and 5R01DA15225-03 from the National Institutes of Health. The Government has certain rights in the invention.

FIELD OF THE INVENTION

The present invention relates generally disorders of the central nervous system and more particularly to alleviating symptoms of Central Nervous System disorders.

BACKGROUND OF THE INVENTION

Central Nervous System disorders are economically and socially devastating. For example, schizophrenia is one of the leading causes of disability worldwide with a lifetime prevalence of 0.6 to 1.3% characterized by high morbidity and mortality. Only less than 15% of people with this disability are competitively employed, whilst about 20% live independently.

Schizophrenia is generally characterized by positive symptoms (such as delusions, hallucinations, disorganized behavior), negative symptoms (such as anergia), affective symptoms (such as dysphoria, hopelessness, anxiety, hostility, aggression) and/or cognitive deficits.

Typical treatment for such disorders includes drugs that affect the monanine receptor systems. For example, the primary effect of first generation antipsychotics is dopamine (D2 receptor) blockade. While these are effective in treating the positive symptoms of schizophrenia, they exert modest effects on negative symptoms and cognitive deficits. Thus, despite the availability of some drugs for treating central nervous system disorders such as schizophrenia, there are many unmet needs for improved methods and compounds for treating central nervous system disorders.

SUMMARY OF THE INVENTION

The invention provides tropane-based prodrug compounds bearing fatty ester and aromatic substituents. The compounds of the present invention generally have the following formula:

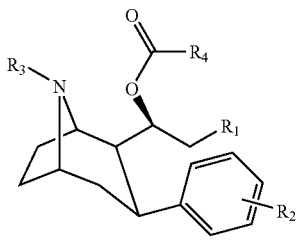

or its enantiomer, and/or racemic mixtures thereof;

where R1 is an alkane or alkene group of three carbons or less; R2 is an alkane group of three carbons or less, a p-methyl, or an adjacent ring at the 2 and 3 positions forming a 2-naphthyl group; R3 is an alkane group of 3 carbons or less; and R4 is an alkane or alkene.

Also provided is a method for using the tropane-based prodrugs to alleviate symptoms of CNS disorders. The method comprises administering to the individual a tropane prodrug in an amount effective to reduce the symptoms of the CNS disorder. Such disease include but are not limited to broad spectrum psychosis such bipolar disorders, depression, mood disorders, addictions, cognitive disorders, and neurodegenerative diseases such as Alzheimer's disease, Parkinson's disease.

DESCRIPTION OF THE INVENTION

This invention provides novel tropane "prodrug" compounds which can be used to alleviate symptoms of CNS disorders via a method also presented herein.

The tropane prodrugs described herein can function as monoamine transporter inhibitors, which have been shown to have significant therapeutic utility in humans. For example, selective serotonin transporter (SERT) inhibitors are some of the most widely used antidepressants. Non selective ligands which bind to SERT as well as to the norepinephrine transporter (NET) have also been launched as antidepressant agents. Dopamine transporter (DAT) inhibitors are used for the treatment of Attention Deficit Disorders (although DAT inhibitors, such as cocaine, can have abuse potential). Thus, monoamine transporter inhibiters have recognized beneficial effects in humans.

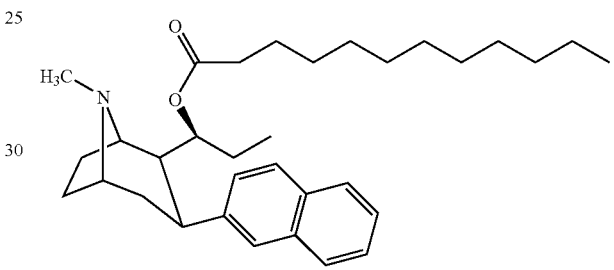

specific example

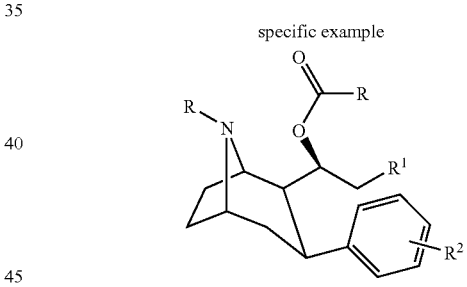

R = long chain hydrocarbon (6C or longer)
general class

Chemistry

The [3+4] cycloaddition between vinyldiazoaceates and pyrroles is a direct method for the synthesis of tropanes and has been extensively used for the synthesis of various 3β-aryltropanes (Scheme 1). Extension of this chemistry allows the synthesis of tropane prodrugs as follows.

Scheme 1

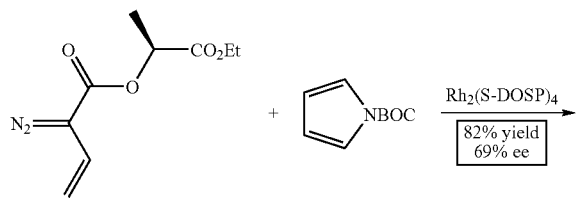

-continued

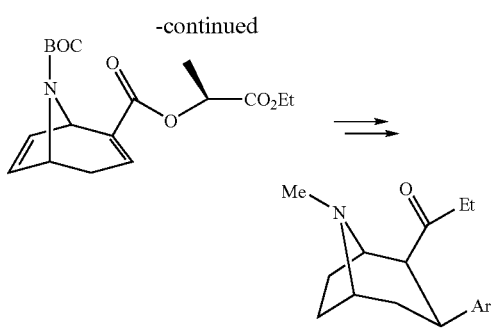

The compounds of the present invention generally have the following formula:

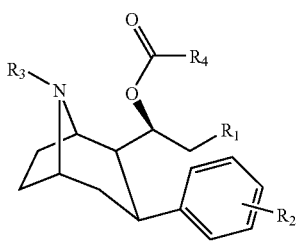

or its enantiomer or racemic mixtures thereof where R1 is an alkane or alkene group of three carbons or less; R2 is an alkane group of three carbons or less, a p-methyl, or an adjacent ring at the 2 and 3 positions forming a 2-naphthyl group; R3 is an alkane group of 3 carbons or less; and R4 is an alkane or alkene.

Preferred are compounds in which R1 and R3 are ethyl and methyl groups respectively, and where R4 is a methyl group or a linear alkane group containing 11 carbons, and where R2 is a p-methyl group or an adjacent ring at the 2 and 3 positions such that the R2-bearing ring comprises a 2-naphthyl group.

Also included in the present inventions are compounds corresponding to the compounds such as described above in which the ester functionality has been replaced with an alcohol (and their enantiomers and racemic mixtures thereof) such as indicated below:

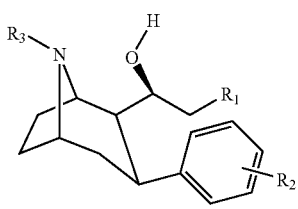

In another embodiment, the present invention provides a method for alleviating symptoms of CNS disorders. The method comprises administering to an individual a composition comprising a tropane prodrug in an amount effective to reduce the symptoms of the CNS disorder.

The method of the invention is suitable for alleviating one or more symptoms of a variety of CNS disorders. Individuals with a CNS disorder frequently exhibit one or more symptoms that are characteristic of the particular disorder. It is also contemplated that a constellation of symptoms from multiple CNS disorders in the same individual can be alleviated by the present method. In this regard, recognizing symptoms from CNS disorders, and determining alleviation of said symptoms during or after practice of the present method is well within the purview of a person having ordinary skill in the art and can be performed using any suitable clinical, diagnostic, observational or other techniques. For example, symptoms of schizophrenia include but are not limited to delusions, hallucinations and catatonic behavior. A reduction in any of these particular symptoms resulting from practicing the method of the invention is considered an alleviation of the symptom. Particular CNS disorders presenting symptoms suitable for alleviation by the present method include but are not limited to broad spectrum psychosis such bipolar disorders, depression, mood disorders, addictions, cognitive disorders, and neurodegenerative diseases such as Alzheimer's disease, Parkinson's disease and combinations thereof. Symptoms of each of these disorders are well known. Recognizing and determining a reduction in the symptoms of any of these particular disorders can be readily performed by those skilled in the art.

Compositions comprising an effective amount of the compound may be administered via any conventional route. Such routes include but are not limited to orally, parenterally, intramuscularly, intravenously and mucosally. In one embodiment the route of administration is oral. Determining a dosage regimen of the compounds is well within the purview of those skilled in the art. By way of example, the dose levels may be from 4 micrograms per kilogram of body weight up to 50 milligrams/Kg of body weight. By way of another example, the dose may be from 20 micrograms/Kg up to 15 mg/Kg. It will be recognized by that dosing parameters, in addition to the weight of the individual, also take into account the age of the individual and the stage of the disease and can be determined according to conventional procedures.

Other components may be combined with the compounds to form pharmaceutical preparations for use in the present method. Such components can be selected depending on factors which include but are not limited to the dosage form, particular needs of the patient, and method of manufacture, among other things. Examples of such components include but are not limited to binders, lubricants, fillers, flavorings, preservatives, colorings, diluents, etc. Additional information regarding pharmaceutical composition components for use with the present method are described in Remington's Pharmaceutical Sciences (18th Edition, A. R. Gennaro et al. Eds., Mack Publishing Co., Easton, Pa., 1990). Accordingly, the selection of particular substances and their compatibilities with the compositions of the present invention can be readily ascertained by those of ordinary skill in the art. Additional details are provided in U.S. Pat. No. 5,763,455, which is incorporated herein by reference.

While the present invention is illustrated by way of the following examples, the examples are meant only to illustrate particular embodiments of the present invention and are not meant to be limiting in any way.

EXAMPLE 1

This Example demonstrates receptor binding properties of compositions of the invention. Binding of at biogenic amine transporters was determined using striatum and frontal cortex dissected from frozen Sprague-Dawley rat brains (Pel-Freez, Rogers, Ark.). Affinities of analogs at dopamine transport sites were determined by displacement of $[^{125}I]$RTI-55 binding in membranes from rat striatum, using 0.5 mg (original wet weight) of membranes and 10 pM $[^{125}I]$RTI-55. Non-specific binding was determined in the presence of 1 μM WF-23 (analog 3a). Affinities of analogs at 5-HT transport sites were determined by displacement of $[^3H]$paroxetine binding in membranes from rat frontal cortex, using 50 mg (original wet weight) of membranes and 0.4 nM [$^3$H]paroxetine. Non-specific binding was determined in the presence of 10 μM fluoxetine. Binding of analogs at norepinephrine transport sites was determined by displacement of [$^3$H]nisoxetine binding in membranes from rat forebrain, using 0.7 nM [$^3$H]nisoxetine. Non-specific binding was determined in the presence of 1 μM desipramine.

Potencies were calculated from displacement curves using 7-10 concentrations of unlabeled analogs, as analyzed by non-linear curve fitting. Because binding of tropanes at dopamine transporters is generally regarded as multiphasic,[1] potencies in inhibiting [$^{125}$I]RTI-55 binding are reported as $IC_{50}$ values. For [$^3$H]paroxetine and [$^3$H]nisoxetine binding assays, $K_i$ values were calculated using the Cheng-Prusoff equation.[2] All data are mean values±S.E.M. of at least three separate experiments, each of which was conducted in triplicate.

The structures for in vitro binding affinities for to DAT and SERT for pro-drugs related to PTT and WF-23 are summarized in Table 1. These compounds display good binding affinities to the transporters and thus are expected to function as slow releasing drugs and to act as long acting agonists.

TABLE 1

| Compound | Code # | IC$_{50}$ DA (nM) | K$_i$ SERT (nM) |
|---|---|---|---|
| 41a | HD-106 | 3.69 | 161 |
| 41b | HD-106 | 6.22 | 588 |
| 42a | HD-108 | 87.9 | >10,000 |
| 42b | HD-109 | 1.72 | 1.06 |
| 43a | HD-110 | 0.891 | 1.91 |
| 43b | HD-111 | 109 | 90.8 | a: Ar = p-tolyl
b: Ar = 2-naphthyl

The foregoing description of the specific embodiments is for the purpose of illustration and is not to be construed as restrictive. From the teachings of the present invention, those skilled in the art will recognize that various modifications and changes may be made without departing from the spirit of the invention.

REFERENCES (1) Madras, B. K.; Fahey, M. A.; Bergman, J.; Canfield, D. R., Spealman, R. D. Effects of cocaine and related drugs in nonhuman primates. I. [$^3$H] Cocaine binding sites in caudate-putamen. *J. Pharmacol. Exp. Ther.* 1989, 251, 132.
(2) Cheng, Y.-C., Prusoff, W. H. Relationship between the inhibition constant (Ki) and the concentration of inhibitor that causes 50 percent inhibition (IC50) of an enzymatic reaction. *Biochem. Pharmacol.* 1973, 22, 3099.

I claim:
1. A compound having one of the following structures:

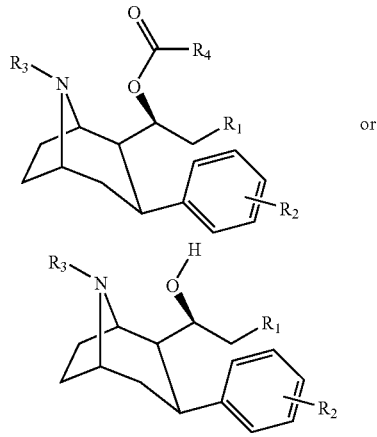

or their enantiomers, or racemic mixtures thereof,
wherein R1, R3 and R4 are hydrogen or alkanes, and R2 is an alkane or an adjacent ring forming a 2-naphthyl group.

2. A compound as in claim 1 wherein
R1 is an alkane or alkene group of three carbons or less;
R2 is an alkane group of three carbons or less, a p-methyl, or an adjacent ring forming a 2-naphthyl group;
R3 is an alkane group of 3 carbons or less; and
R4 is an alkane or alkene.

3. A compound as in claim 1 wherein R4 is an alkane or alkene of three carbons or more.

4. A compound as in claim 1 wherein R4 is an alkane or alkene of six carbons or more.

5. A compound as in claim 4 wherein
R1 is ethyl;
R2 is a p-methyl;
R3 is a methyl; and
R4 is hydrogen or a linear alkane of 11 carbons.

6. A compound as in claim 1 wherein
R1 is ethyl;
R2 is an adjacent ring forming a 2-naphthyl group;
R3 is a methyl; and
R4 is a hydrogen or methyl.

7. A compound as in claim 6 wherein
R1 is ethyl;
R2 is a p-methyl;
R3 is a methyl; and
R4 is a hydrogen or linear alkane of 11 carbons.

8. A compound as in claim 1 wherein
R1 is ethyl;
R2 is an adjacent ring forming a 2-naphthyl group;
R3 is a methyl; and
R4 is a hydrogen or methyl.

* * * * *